US010266455B2

(12) United States Patent
Schutte et al.

(10) Patent No.: US 10,266,455 B2
(45) Date of Patent: Apr. 23, 2019

(54) COATING SUITABLE FOR MEDICAMENT CONTACT

(75) Inventors: Grant Schutte, Pittsburgh, PA (US); Robert M. O'Brien, Monongahela, PA (US)

(73) Assignee: The Sherwin-Williams Company, Cleveland, OH (US)

( * ) Notice: Subject to any disclaimer, the term of this patent is extended or adjusted under 35 U.S.C. 154(b) by 1222 days.

(21) Appl. No.: 12/746,276

(22) PCT Filed: Dec. 4, 2008

(86) PCT No.: PCT/US2008/085544
§ 371 (c)(1),
(2), (4) Date: Jun. 4, 2010

(87) PCT Pub. No.: WO2009/073791
PCT Pub. Date: Jun. 11, 2009

(65) Prior Publication Data
US 2010/0282248 A1  Nov. 11, 2010

Related U.S. Application Data

(60) Provisional application No. 61/012,210, filed on Dec. 7, 2007, provisional application No. 61/088,767, filed on Aug. 14, 2008.

(51) Int. Cl.
| | | |
|---|---|---|
| *A61M 11/00* | (2006.01) | |
| *A61M 15/00* | (2006.01) | |
| *B05D 3/00* | (2006.01) | |
| *G01F 11/00* | (2006.01) | |
| *C04B 41/52* | (2006.01) | |
| *B65B 55/24* | (2006.01) | |
| *A61F 2/00* | (2006.01) | |
| *C03C 17/22* | (2006.01) | |
| *A61B 50/30* | (2016.01) | |

(52) U.S. Cl.
CPC .............. *C04B 41/52* (2013.01); *A61B 50/30* (2016.02); *A61F 2/0095* (2013.01); *B65B 55/24* (2013.01); *C03C 17/22* (2013.01); *A61M 15/009* (2013.01); *Y10T 428/13* (2015.01)

(58) Field of Classification Search
CPC .. C09D 125/14; C09D 133/02; C09D 133/01; C09D 163/00; C09D 5/44; C08L 27/12; C08L 63/00; B05D 1/02; B05D 3/007; A61K 9/008; A61K 9/12
USPC ............ 128/200.11, 200.12, 200.23, 203.12; 428/34.1, 35.7, 35.8
See application file for complete search history.

(56) References Cited

U.S. PATENT DOCUMENTS

| | | | |
|---|---|---|---|
| 3,991,216 A | 11/1976 | Christenson et al. | |
| 4,289,674 A | 9/1981 | Christenson et al. | |
| 4,335,030 A * | 6/1982 | Concannon | 523/408 |
| 4,446,258 A | 5/1984 | Chu et al. | |
| 4,476,262 A | 10/1984 | Chu et al. | |
| 5,776,433 A * | 7/1998 | Tzou et al. | 424/45 |
| 5,830,952 A | 11/1998 | Pedersen et al. | |
| 5,869,552 A | 2/1999 | Pedersen et al. | |
| 5,980,867 A | 11/1999 | Tzou et al. | |
| 6,253,762 B1 | 7/2001 | Britto | |
| 6,596,260 B1 | 7/2003 | Brugger et al. | |
| 6,610,273 B2 | 8/2003 | Wu et al. | |
| 6,730,361 B2 | 5/2004 | Parekh et al. | |
| 7,037,584 B2 | 5/2006 | Wind et al. | |
| 7,189,717 B2 | 3/2007 | Yasuda et al. | |
| 7,205,026 B2 | 4/2007 | Groeger et al. | |
| 2001/0004892 A1* | 6/2001 | Datta et al. | 128/200.14 |
| 2002/0043262 A1 | 4/2002 | Langford et al. | |
| 2003/0121793 A1 | 7/2003 | Groeger et al. | |
| 2003/0207057 A1 | 11/2003 | Britto et al. | |
| 2004/0071906 A1 | 4/2004 | Brewis et al. | |
| 2004/0134824 A1* | 7/2004 | Chan et al. | 206/524.1 |
| 2004/0259989 A1* | 12/2004 | O'Brien et al. | 524/236 |
| 2005/0022806 A1* | 2/2005 | Beaumont et al. | 128/200.14 |
| 2006/0083879 A1 | 4/2006 | Brewis et al. | |
| 2006/0100366 A1* | 5/2006 | O'Brien et al. | 524/800 |
| 2006/0141261 A1* | 6/2006 | Wind et al. | 428/413 |
| 2007/0025920 A1 | 2/2007 | Lewis et al. | |
| 2007/0087146 A1 | 4/2007 | Evans et al. | |
| 2007/0088102 A1 | 4/2007 | Knouse | |
| 2007/0117928 A1 | 5/2007 | O'Brien et al. | |
| 2009/0145427 A1 | 6/2009 | Groeger et al. | |

FOREIGN PATENT DOCUMENTS

| | | |
|---|---|---|
| EP | 1131051 B1 | 1/2006 |
| GB | 2328932 A | 3/1999 |
| WO | 9517195 A1 | 6/1995 |
| WO | 9632345 A1 | 10/1996 |
| WO | 0151222 A1 | 7/2001 |
| WO | 2004093950 A1 | 11/2004 |
| WO | 2008036628 A2 | 3/2008 |

OTHER PUBLICATIONS

Koleske, J.V., Paint and Coating Testing Manual: Fourteenth Edition of the Gardner-Sward Handbook. Philidelphia: ASTM, 1995, p. 717.*
The Dictionary of Food Science and Technology. Chinchester, U.K. Wiley-Blackwell, 2009, p. 30.*
International Search Report and Written Opinion dated Feb. 4, 2009 for International Application PCT/US2008/085544 (8 pages).
"FEP Coated Inhaler Cans MDI—Packing Products—IntraPac." Intrapac International, <http://www.intrapacinternational.com/products/other/fep-coating-mdi.aspx> (accessed Apr. 13, 2015).
"BPA-NI Can Coatings", Grace Materials Technologies, W.R. Grace & Co., 2013, Asia Can Tech 2013 presentation. (24 pages).

(Continued)

*Primary Examiner* — Lee E Sanderson

(57) ABSTRACT

A coating composition is provided that is suitable for use on a medicament-contact surface. The coating composition preferably includes one or more acrylic-containing polymer and a carrier. In preferred embodiments, the coating composition is an aqueous dispersion or solution.

21 Claims, No Drawings

(56) References Cited

OTHER PUBLICATIONS

"Leading in Inhalation Component Technology," 3M Health Care Limited, Clitheroe Site, 2008. (7 pages).
"Latexes," Organic Coatings: Science and Technology, vol. 1: Film Formation, Components and Appearance, Chapter 5, A Wiley-Interscience Publication, John Wiley & Sons, Inc. 1992. (3 pages).

* cited by examiner

COATING SUITABLE FOR MEDICAMENT CONTACT

CROSS REFERENCE TO RELATED APPLICATION

This application is the National Stage filing under 35 U.S.C. 371 of International Application No. PCT/US2008/085544 filed on Dec. 4, 2008, which claims priority to U.S. Provisional Application No. 61/012,210 filed on Dec. 7, 2007 and U.S. Provisional Application No. 61/088,767 filed on Aug. 14, 2008, the disclosures of which are incorporated herein by reference in their entirety.

TECHNICAL FIELD

This invention relates to polymer coating compositions. More specifically, the invention relates to polymer coating compositions suitable for use on surfaces intended for contact with a medicament.

BACKGROUND

Various articles are used for the storage and/or administration of medicaments. Such articles include one or more surfaces that come into contact with the medicament, often for prolonged times. For example, drug-dispensing articles such as metered dose inhalers ("MDIs") typically have a container for storing aerosol medicaments. Traditionally, these containers have been formed from metal (e.g., aluminum) and have a bare metal inner surface for contacting the medicament. These metal surfaces have typically suffered from several drawbacks which include, for example, adsorption of drug onto the metal surfaces (which can result in inconsistent or reduced drug delivery), reduced drug stability, and possible contamination of the drug (e.g., through extraction of residual organic compounds present on the metal surface). Despite these shortcomings, however, bare metal surfaces are still widely used for medicament containers such as MDI cans.

To address some of these shortcomings, polymer coatings such as fluoropolymers have been used as protective coatings for the inner surfaces of MDI cans to prevent interaction between medicament and an underlying metal substrate. These polymer coatings have tended to be solvent based. Although water-based fluoropolymer systems have been developed, these systems have typically required costly surface modifications prior to application.

What is needed in the marketplace is an improved polymer coating composition, and particularly an improved water-based coating composition for use in coating substrates exposed to medicaments.

SUMMARY

In formulating a polymer coating for use in coating a medicament-contact surface, the challenge for the coating designer is to balance a variety of coating characteristics such as chemical resistance, adhesion to the underlying substrate, low migration of components of the coating into medicament mixtures, low drug adsorption onto the coating, suitable compatibility with medicament compounds, stability, and cost.

In one aspect, the invention provides a coating composition suitable for use on a medicament-contact surface. The coating composition preferably includes a resin system and a carrier, and may also include one or more additional ingredients such as, for example, a crosslinker. The resin system preferably includes an acrylic-containing polymer. In some embodiments, the coating composition constitutes an aqueous dispersion or solution that includes a water-dispersible resin system having an acrylic-containing polymer and one or more optional co-resins. The one or more co-resins may be present in the acrylic-containing polymer itself or may be present as a separate material blended with the acrylic-containing polymer. In certain embodiments, the resin system includes a water-dispersible acrylic-containing polymer in the form of an epoxy-acrylate polymer, a polyester-acrylate polymer, an acrylic-acrylate polymer, an emulsion polymerized acrylic latex polymer, or a mixture thereof.

In another aspect, the invention provides an article having a coating composition described herein applied to at least a portion of a medicament-contact surface. The article may include a container for storing or administering a medicament, where the container includes a cured coating of the invention applied to an inner surface of the container. In a presently preferred embodiment, the article is a metal MDI can coated on its inner surface with a cured coating of the invention.

In another aspect, the invention provides a method of coating a substrate with a coating composition described herein. A coating composition is prepared and applied to a medicament-contact surface of the substrate. The coating composition can be applied to the substrate either prior to, or after, forming the substrate into an article such as, for example, a container. In preferred embodiments, the coating composition is cured to form an adherent cured coating on the substrate.

In another aspect, the invention provides a method of using an article, which includes providing a container having an adherent coating described herein applied on a medicament-contact surface of the container and filling the container with, for example, a medicament, a propellant, or a mixture of medicament and propellant. In one embodiment, an MDI container having an adherent coating of the invention applied on a medicament-contact surface of the container is filled with a composition containing (i) an MDI-administered medicament such as albuterol, salmeterol, and/or budesonide and (ii) a propellant.

Selected Definitions

Unless otherwise specified, the following terms as used herein have the meanings provided below.

The term "medicament" refers to a therapeutic substance that is intended for intake (via any delivery route) by humans or animals. The term "intake" as used in this context includes, for example, medicaments suitable for internal use, as well as medicaments suitable for topical application.

The term "medicament-contact surface" refers to the substrate surface of an article that is in contact with, or intended for contact with, a medicament. For example, an interior surface of a container such an MDI can is a medicament-contact surface.

The term "metered dose inhaler" or "MDI" includes both pressurized and non-pressurized MDIs.

The term "on", when used in the context of a coating applied on a surface or substrate, includes both coatings applied directly or indirectly to the surface or substrate. Thus, for example, a coating applied to a primer layer overlying a substrate constitutes a coating applied on the substrate.

The term "substantially free" of a particular mobile compound means that the compositions of the present invention contain less than 100 parts per million (ppm) of the recited mobile compound.

The term "essentially free" of a particular mobile compound means that the compositions of the invention contain less than 10 ppm of the recited mobile compound.

The term "essentially completely free" of a particular mobile compound means that the compositions of the invention contain less than 1 ppm of the recited mobile compound.

The term "completely free" of a particular mobile compound means that the compositions of the invention contain less than 20 parts per billion (ppb) of the recited mobile compound.

If the aforementioned phrases are used without the term "mobile" (e.g., "substantially free of XYZ compound") then the compositions of the invention contain less than the aforementioned amount of the compound whether the compound is mobile in the coating or bound to a constituent of the coating.

The term "mobile" means that the compound can be extracted from the cured coating when a coating (typically ~1 mg/cm2 (6.5 mg/in2) thick) is exposed to a test medium for some defined set of conditions, depending on the end use. An example of these testing conditions is exposure of the cured coating to HPLC-grade acetonitrile for 24 hours at 25° C.

The term "polymer" includes both homopolymers and copolymers (i.e., polymers of two or more different monomers).

The term "comprises" and variations thereof do not have a limiting meaning where these terms appear in the description and claims.

The term "crosslinker" refers to a molecule capable of forming a covalent linkage between polymers or between two different regions of the same polymer.

The term "water-dispersible" in the context of a water-dispersible polymer means that the polymer can be mixed into water (or an aqueous carrier) to form a stable mixture. For example, a mixture that readily separates into immiscible layers is not a stable mixture. The term "water-dispersible" is intended to include the term "water-soluble." In other words, by definition, a water-soluble polymer is also considered to be a water-dispersible polymer.

The term "dispersion" in the context of a dispersible polymer refers to the mixture of a dispersible polymer and a carrier. The term "dispersion" is intended to include the term "solution."

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges by endpoints include all numbers subsumed within that range (e.g., 1 to 5 includes 1, 1.5, 2, 2.75, 3, 3.80, 4, 5, etc.). Furthermore, disclosure of a range includes disclosure of all sub-ranges included within the broader range (e.g., 1 to 5 discloses 1 to 4, 1.5 to 4.5, 1 to 2, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the description below. Other features, objects, and advantages of the invention will be apparent from the description and the claims.

DETAILED DESCRIPTION

In one aspect, the invention provides a coating composition suitable for forming adherent coatings on surfaces that may contact medicaments. The coating composition preferably includes a film-forming resin system and a carrier. The resin system may be dispersed or dissolved in a suitable carrier to yield a coating composition. Any suitable carrier may be used including, for example, an aqueous carrier, an organic solvent, or a mixture thereof. In preferred embodiments, the coating composition is an aqueous dispersion of a water-dispersible resin system.

The resin system preferably includes an efficacious amount of one or more acrylic-containing film-forming polymers. In some embodiments, the resin system includes both an acrylic-containing polymer and one or more co-resins, which can be present, for example, as (i) separate polymers in a blend, (ii) different portions of a single polymer, or (iii) mixtures thereof. Suitable co-resins may include polyester polymers, epoxy polymers, fluoropolymers, phenolic resins, vinyl chloride polymers (e.g., polyvinyl chloride, "PVC"), acrylic polymers, and combinations thereof.

In certain preferred embodiments, the acrylic-containing polymer includes both an acrylic component, typically in the form of an acrylic polymer, and a co-resin component such as, for example, an epoxy polymer, an additional acrylic polymer component, or a polyester polymer. Non-limiting examples of such acrylic-containing polymers include epoxy-acrylate polymers, polyester-acrylate polymers, acrylic-acrylate polymers, and emulsion polymerized acrylic latex polymers discussed in further detail below.

Preferred embodiments of the coating composition are particularly suited for use on surfaces that may come into contact with medicaments for prolonged periods of time (e.g., days, weeks, months, and/or years). For coatings to be suitable for use in rigorous medicament-contact applications, the coatings must typically exhibit a combination of stringent properties that are difficult to achieve. These properties include, for example, (A) low migration of compounds from the coating and/or an underlying substrate into the medicament, (B) good adhesion to an underlying substrate, (C) low levels of drug deposition and adherence, (D) good chemical resistance (e.g., to protect the underlying substrate from the medicament and the medicament from the underlying substrate), and (E) high levels of drug stability for medicament contacting the coating. Preferred cured coatings of the invention exhibit all of these properties.

Propellant-based medicaments are typically intended for intake via aerosol inhalation into the lungs or nasal passages. Propellant-based medicaments such as, for example, those administered by pressurized MDIs, tend to be particularly harsh on polymer coatings. As such, conventional polymer coatings typically do not exhibit the balance of stringent coating properties desired for this demanding end use. Preferred cured coatings of the invention, however, are well suited for use on metal surfaces (e.g., aluminum) that come into prolonged contact with propellant-based medicaments.

Certain preferred cured coating compositions of the invention are particularly suited for prolonged contact with the types of medicament compositions frequently administered using MDIs. Medicament compositions administered via MDIs typically include a drug (e.g., a pulmonary or nasal medicament) as a suspension or a solution in a liquid carrier. Some examples of such drugs include albuterol, salmeterol, budesonide, alone or in combination with orther active ingredients. For pressurized MDIs ("pMDIs"), the carrier is typically a liquefied gas propellant such as, for example, a hydrofluoroalkane ("HFA"), chlorofluorocarbon ("CFC"), or hydro-fluorocarbon ("HFC"). Propellants used in pMDIs typically have boiling points that range from about −25° C. to about 25° C. For pMDIs, the medicament composition is typically stored in a sealed container capable of withstanding the pressure required to maintain the propellant as a liquid. The medicament composition is typically dispensed from the container by activation of a dose-metering valve.

It was a surprising and unexpected result that cured coating compositions of the invention containing an efficacious amount of film-forming acrylic-containing polymer, when applied and cured on the inner surface of cleaned deep-drawn aluminum pMDI cans, exhibited comparable coating performance properties to conventional cured solvent-based fluoropolymer coatings. Preferred cured coatings of the invention, when present on an inner surface of an aluminum pMDI can packed with a propellant-based medicament, exhibited all of the features (A)-(E) described above.

The acrylic portion(s) of the acrylic-containing polymer of the invention is preferably prepared through chain-growth polymerization using one or more acrylic monomers as reactants. Suitable acrylic monomers include (meth)acrylate compounds, vinyl monomers and the like, and combinations thereof. Examples of suitable (meth)acrylate compounds (or monomers) include those having the structure: $C(HR_1)=C(R_2)-CO-OR_3$, wherein $R_1$ is hydrogen (preferred), a methyl group, or a substituted or unsubstituted alkyl group (including, e.g., carboxylic acid groups) preferably having one to five carbon atoms; $R_2$ is a hydrogen or a methyl group; and $R_3$ is a hydrogen or a substituted or unsubstituted alkyl group preferably containing one to sixteen carbon atoms. The $R_3$ group can be substituted with one or more, and typically one to three, moieties such as hydroxy, halo, amino, phenyl, and alkoxy, for example. Suitable (meth)acrylate compounds, therefore, encompass hydroxy alkyl (meth)acrylates and aminoalkyl (meth)acrylates. Suitable (meth)acrylate compounds can be an ester of acrylic or methacrylic acid wherein $R_3$ is a substituted or unsubstituted alkyl group containing one to sixteen carbon atoms. Examples of suitable (meth)acrylic acid esters are C1-C24 alkyl esters or cycloalkyl esters of acrylic or methacrylic acids, such as methyl acrylate, ethyl acrylate, propyl acrylate, isopropyl acrylate, n-butyl acrylate, isobutyl acrylate, t-butyl acrylate, hexyl acrylate, 2-ethylhexyl acrylate, n-octyl acrylate, decyl acrylate, stearyl acrylate, lauryl acrylate, cyclohexyl acrylate, methyl methacrylate, ethyl methacrylate, n-propyl methacrylate, isopropyl methacrylate, n-butyl methacrylate, isobutyl methacrylate, t-butyl methacrylate, hexyl methacrylate, 2-ethylhexyl methacrylate, octyl methacrylate, decyl methacrylate, lauryl methacrylate, stearyl methacrylate, cyclohexyl methacrylate, etc.; C2-C18 alkoxyalkyl esters of acrylic or methacrylic acids, such as methoxybutyl acrylate, methoxybutyl methacrylate, methoxyethyl acrylate, methoxyethyl methacrylate, ethoxybutyl acrylate, ethoxybutyl methacrylate, etc.; and mixtures thereof. Examples of presently preferred (meth)acrylates include acrylic acid, methacrylic acid, and ethyl acrylate.

Examples of suitable vinyl monomers include styrene, halostyrene, isoprene, diallylphthalate, divinylbenzene, conjugated butadiene, alpha-methylstyrene, vinyl toluene, vinyl naphthalene and the like, and mixtures thereof. Other suitable polymerizable vinyl monomers can include acrylamide, methacrylamide (or their methylol or etherified methylol derivatives), acrylonitrile, methacrylonitrile, vinyl acetate, vinyl propionate, vinyl butyrate, vinyl stearate, isobutoxymethyl acrylamide and the like, and mixtures thereof. Styrene is a preferred vinyl monomer.

In certain embodiments, the acrylic-containing polymer may include oxirane-functional ethylenically unsaturated monomers. Suitable such monomers may include the glycidyl ester of any of the ethylenically unsaturated mono- or mult-functional acids described herein. Glycidyl (meth)acrylate is presently preferred.

The combination and/or ratio(s) of the above monomers may be adjusted to provide a desired coating or film property. Preferably, at least a portion of the above monomers are capable of rendering the acrylic-containing polymer dispersible in an aqueous carrier. Examples of such monomers include monomers having salt groups or salt-forming groups. For example, acid-functional monomers that form salt groups upon neutralization with a base may be used. Non-limiting examples of such acid-functional monomers include acrylic acid, methacrylic acid, fumaric acid, crotonic acid, maleic acid, itaconic acid and the like, anhydrides thereof, and mixtures thereof. Presently preferred acid-functional monomers include acrylic acid, methacrylic acid, and mixtures thereof.

The acrylic-containing polymer and/or the overall resin system of the coating composition can include any suitable level of acrylic to achieve the desired result. The acrylic-containing polymer preferably includes at least about 5 weight percent ("wt-%") of acrylic, more preferably at least about 10 wt-% of acrylic, and even more preferably at least about 15 wt-% of acrylic. In some embodiments, the acrylic-containing polymer may include more than 40 wt-% of acrylic. In certain preferred embodiments, the acrylic-containing polymer includes from about 50 wt-% to about 100 wt-% of acrylic or from about 75 wt-% to about 100 wt-% of acrylic. The aforementioned acrylic weight percents may be determined by considering the total weight of acrylic monomer (e.g., (meth)acrylate and vinyl monomer) included in the acrylic-containing polymer.

A polymer is not considered to include any acrylic unless it includes at least some (meth)acrylate compound. Thus for example, a polymer that includes vinyl monomer, but does not include (meth)acrylate monomer, is not considered to include any wt-% acrylic. If, however, a polymer includes (meth)acrylate monomer, then the acrylic wt-% of the polymer includes both the (meth)acrylate monomer and any other acrylic co-monomers such as, for example, vinyl monomers present in the polymer.

The wt-% of acrylic in the overall resin system (based on total solids of the resin system) may be similar or different to that described above for the acrylic-containing polymer, depending upon the other materials (if any) included in the resin system in addition to the acrylic-containing polymer.

Preferably, the resin system includes at least from about 10 to about 15 wt-% of acrylic, based on total solids of the resin system. In some embodiments, the resin system may include up to about 100 wt-% of acrylic, based on the total solids of the resin system.

The number of acid groups, if any, included in the acrylic portions of the acrylic-containing polymer may be adjusted according to a variety of factors, including, for example, whether other portions (e.g., non-acrylic portions) of the polymer include moieties that assist in dispersing the polymer in aqueous carriers. (For sake of convenience, the cumulative acrylic portion(s) of the acrylic-containing polymer are referred to as the "acrylic component." Thus, for example, if 50 wt-% of the acrylic-containing polymer is acrylic, the acrylic component constitutes 50 wt-% of the acrylic-containing polymer.) In preferred embodiments, the acrylic component of the acrylic-containing polymer includes an amount of acid-functional (or anhydride-functional) acrylic monomer of preferably at least about 10 wt-%, more preferably at least about 15 wt-%, and even more preferably at least about 20 wt-%, based on the total weight of the acrylic monomer mixture used to form the acrylic component. In preferred embodiments, the acrylic component includes an amount of acid-functional (or anhydride-functional) acrylic monomer of preferably less than about 90 wt-%, more preferably less than about 85 wt-%, and even more preferably less than about 80 wt-%, based on the total weight of the acrylic monomer mixture used to form the acrylic component.

A presently preferred acrylic monomer mixture for forming the acrylic component includes a (meth)acrylic acid ester, an ethylenically unsaturated mono- or multi-functional acid or anhydride, and an optional vinyl compound. In a specific presently preferred embodiment, the acrylic component is a reaction product of an acrylic and/or methacrylic acid, styrene, and ethyl acrylate.

Examples of suitable neutralizing agents for rendering the acrylic-containing polymer water-dispersible include neutralizing bases such as a primary, secondary or tertiary amine; a primary, secondary or tertiary alkanolamine; ammonium; an alkylammonium hydroxide; an arylammonium hydroxide; or mixtures thereof. Examples of suitable neutralizing bases include ammonium hydroxide, a tetraalkylammonium hydroxide (wherein an alkyl group has preferably 1 to about 4 carbon atoms—e.g., tetramethylammonium hydroxide), monoethanolamine, dimethylamine, methyldiethanolamine, benzylamine, diisopropylamine, methylethanolamine, butylamine, piperazine, dimethylethanolamine, diethylethanolamine, diethanolamine, morpholine, N-methylmorpholine, N-ethylmorpholine, triethylamine, 2-dimethylamine-2-methyl-1-propanol, diisopropanolamine, trimethylamine, N-methylpiperidine, 2-amino-2-methyl-1-propanol, piperidine, pyridine, dimethylaniline, and similar amines and alkanolamines, and mixtures thereof.

Acrylic-containing polymers of the invention may exhibit any suitable acid number. Acid numbers are typically expressed as milligrams of KOH required to titrate a sample to a specified end point. Methods for determining acid numbers are well known in the art. See, for example, ASTM D 974-04 entitled "Standard Test Method for Acid and Base Number by Color-Indicator Titration" and available from the American Society for Testing and Materials International of West Conshohocken, Pa. In presently preferred embodiments, the acrylic-containing polymer has an acid number of at least about 10, more preferably at least about 20, and even more preferably at least about 25. The acid number of the acrylic-containing polymer is preferably less than about 200, more preferably less than about 150, and even more preferably less than about 100.

In certain embodiments where the coating composition is a solvent-based coating composition, the acid number of the acrylic-containing polymer may be different from that discussed in the preceding paragraph.

In certain embodiments where the acrylic-containing polymer is a copolymer of an acrylic polymer and a co-resin, the acrylic polymer preferably has a number average molecular weight ($M_n$) of at least about 2,000, more preferably at least about 3,000. In such embodiments, the acrylic polymer preferably has a $M_n$ of less than about 10,000, more preferably less than about 8,000, and even more preferably less than about 7,000. Examples of such embodiments include certain epoxy-acrylate, acrylic-acrylate, and polyester-acrylate polymers described herein.

As previously discussed, in certain embodiments, the acrylic-containing polymer of the invention may be an acrylic-acrylate polymer, an epoxy-acrylate polymer, an emulsion polymerized acrylic latex polymer, or a polyester-acrylate polymer. Further discussion of such embodiments is provided below.

In certain embodiments, the acrylic-containing polymer of the invention is an epoxy-acrylate copolymer that includes both an acrylic polymer and an epoxy polymer. The epoxy polymer is preferably formed from an epoxy compound that contains at least one epoxy group. The epoxy compound preferably has an average of between about 1 to about 3 epoxy groups per molecule of the epoxy compound, more preferably between about 1.5 to about 2.5 epoxy groups per molecule of the epoxy compound, and even more preferably of between about 1.6 to about 2.0 epoxy groups per molecule of the epoxy compound. The epoxy compound may be described, in part, by its epoxy equivalent weight ("EEW"). Suitable epoxy compounds typically have an EEW of preferably at least about 1,000, more preferably at least about 1,500, and even more preferably at least about 2,500. Moreover, suitable epoxy compounds typically have an EEW of preferably less than about 25,000, more preferably less than about 22,500, and even more preferably less than about 20,000. In some embodiments, suitable epoxy compounds have an EEW of less than about 3,800.

The epoxy compound can be any suitable epoxy compound to elicit a desired coating or film property. In certain preferred embodiments, the epoxy compound is a linear epoxy resin with one or more terminal epoxy (or oxirane) groups. The epoxy compound may be aliphatic or aromatic. In some embodiments, suitable epoxy compounds may include aromatic compounds such as, for example, epoxy resins based on the diglycidyl ether of bisphenol A ("BADGE"). The epoxy compound can be used in a commercially available form, or can be prepared by advancing a low-molecular-weight epoxy compound by standard methods. For example, an epoxy compound having an EEW of about 180 to about 500 can be advanced with a suitable amount of a dihydric phenol (e.g., bisphenol A ("BPA")) to produce an epoxy compound having an EEW of between about 1,000 and about 12,000. Alternatively, any suitable difunctional compound (or mixture of compounds) capable of reacting with oxirane groups may be employed. Examples of such compounds may include diacids such as, e.g., sebacic, adipic, azelaic, and dimer fatty acids (e.g., saturated and/or unsaturated dimer fatty acids, more preferably saturated); amines such as, e.g., ethanolamine and/or butylamine; amino acids such as, e.g., alanine, lysine, and aminododecanoic acid; diols; and mixtures and variations thereof.

In some embodiments, the epoxy compound may be upgraded using non-BPA-containing dihydric phenols (e.g., bis-4-hydroxy benzoate of 1,4-cyclohexane dimethanol) such as, for example, those described in U.S. Pat. App. No. 2007/0087146, which is incorporated herein by reference. In some such embodiments where an epoxy compound free of BPA is upgraded, the resulting epoxy compound is free of both bound and extractible BPA. Thus, in certain embodiments, the coating composition of the invention may be substantially free, or more preferably completely free, of mobile and/or bound BPA and aromatic glycidyl ether compounds Examples of suitable epoxy compounds may include the DER 331, DER 664, DER 667, DER 668, and DER 669 products (all commercially available from Dow Chemical Co., Midland, Mich.); and the EPON 828, EPON 1001, EPON 1004, EPON 1007, and EPON 1009 products (all commercially available from Hexion Specialty Chemical, Houston, Tex.). Depending upon the material and the desired properties, the epoxy compounds may be used in their commercial form or advanced, e.g., with a dihydric phenol (e.g., BPA).

The amount of epoxy compound included may vary widely depending upon the desired result. When the acrylic-containing polymer is an epoxy-acrylate polymer, it preferably includes an amount of epoxy compound (after any optional upgrading) of at least about 5 wt-%, more preferably at least about 25 wt-%, and even more preferably at least about 50 wt-%. The epoxy-acrylate polymer preferably includes an amount of epoxy compound (after any optional upgrading) of less than about 95 wt-%, more preferably less than about 90 wt-%, and even more preferably less than about 87 wt-%.

Any suitable epoxy-acrylate polymer may be used. Preferably, the epoxy-acrylate polymer is a reaction product of an epoxy polymer and an acrylic polymer, which may be facilitated through the presence of an amine, and more preferably a tertiary amine.

Suitable epoxy-acrylate polymers can be formed, for example, using the processes described in U.S. Pat. Nos. 4,446,258, 4,476,262, and 7,037,584, which are incorporated herein by reference. While not intending to be bound by theory, these references describe, in part, epoxy-acrylate polymers that can be formed via quaternary ammonium salts formed through reaction of oxirane groups, carboxylic acid groups, and amines (preferably tertiary amines). Thus, for example, in one embodiment, a suitable water-dispersible epoxy-acrylate polymer can be formed from preformed polymers (e.g., an oxirane-functional epoxy polymer and an acid-functional acrylic polymer) reacted in the presence of an amine (preferably a tertiary amine). In another embodiment, a water-dispersible epoxy-acrylate polymer is formed from a preformed epoxy polymer that is reacted with monomers for the acrylic component in the presence of an amine (preferably a tertiary amine). In another embodiment, a water-dispersible epoxy acrylate polymer is formed from a reaction mixture in which the epoxy polymer is formed in situ, and then reacted in the presence of an amine (preferably a tertiary amine) with either (i) monomers for the acrylic component and/or (ii) preformed acrylic polymer. If desired, an acid-functional acrylic polymer can be combined with an amine (more preferably a tertiary amine) to at least partially neutralize it prior to reaction with an epoxy polymer.

While the exact mode of reaction is not fully understood, it is believed that a competition between two reactions exists. While not intending to be bound by theory, one reaction is believed to involve the tertiary amine first reacting with the acrylic polymer forming an amine-neutralized ion which can then react with the epoxy polymer. A second reaction may involve the free tertiary amine reacting directly with the epoxy polymer. In either case, the respective products formed are the hydroxy ester of the epoxy polymer with the acrylic polymer and a polymeric quaternary ammonium-amine mixed salt (from the tertiary amine, epoxy polymer, and the acrylic polymer). Reaction conditions, including the presence of water as a reaction modifier, can be chosen to favor either the esterification or quaternization reaction. A high level of quaternization is believed to improve water-dispersibility and/or compatibilization of the epoxy and acrylic components of the resin system, while a high level of esterification is believed to give higher viscosity and possibly gel-like material. By varying the ratio of the reactants and reaction conditions, the solids content, viscosity, particle size and application properties of the product can be varied over a wide range.

The amount of amine used may vary widely. Preferably at least about 0.1 percent by weight, and more preferably at least about 0.3 percent by weight of the amine, based on the total weight of epoxy polymer and the acrylic polymer, is used. Preferably, no greater than about 10 percent by weight of the amine, based on the total weight of epoxy polymer and the acrylic polymer, is used. Non-limiting example of suitable amines for use in facilitating the reaction include, for example, tertiary amines such as dimethylethanolamine, dimethylbenzylamine, trimethylamine, tributylamine, and the like. A presently preferred tertiary amine is dimethylethanolamine.

It is contemplated that suitable epoxy-acrylate polymers may also be formed using, for example, some of the techniques disclosed in U.S. Pat. Nos. 5,830,952, 5,869,552 and 5,922,817, which are incorporated herein by reference. Thus for example, in some embodiments, the resin system may include a graft polymer having one or more pendant groups attached to a backbone. In one embodiment, a backbone of the graft polymer includes one or more acrylic oligomers or polymers with one or more pendant epoxy components attached to the backbone. A linking group may optionally be included to covalently link the epoxy component and the acrylic component through the linking group.

Suitable linking groups are described in the aforementioned patents. Typically, a compound used to form the linking group includes at least two functional groups. In a preferred embodiment, the linking compound is a polyfunctional monomer with a functional group (e.g., a carboxylic group, an amine group, an amide group, etc.) capable of reacting with an epoxy group and a second functional group (e.g., a carbon-carbon double or triple bond or an allylic or double allylic hydrogen) capable of reacting with an acrylic component.

In such embodiments, the acrylic component may be reacted with the linking compound using any suitable reaction, including, for example, (i) hydrogen extraction to form a covalent linkage and/or (ii) direct addition to a carbon-carbon double or triple bond of the linking compound. While not intending to be bound by theory, the use of one or more free-radical initiators (e.g., such as benzoyl peroxide) may contribute to grafting of acrylic components and epoxy components through proton extraction.

In certain preferred embodiments, the acrylic-containing polymer of the resin system comprises an emulsion polymerized acrylic latex polymer. See, for example, U.S. Patent App. No. 2006/0100366, which describes, in part, suitable emulsion polymerized acrylic latex polymers. By way of example, a suitable emulsion polymerized acrylic latex polymer may be formed by:
(a) forming a salt of an acid- or anhydride-functional polymer (preferably an acrylic polymer) and an amine (preferably a tertiary amine such as described elsewhere herein) in a carrier comprising water to form an aqueous dispersion;
(b) combining an ethylenically unsaturated monomer component comprising 0.1 wt-% to 30 wt-% (more preferably 1 to 10 wt-%) of an oxirane-functional alpha, beta-ethylenically unsaturated monomer (e.g., glycidyl (meth)acrylate) with the aqueous dispersion, based on the weight of the monomer component; and
(c) polymerizing the ethylenically unsaturated monomer component in the presence of the aqueous dispersion to form an emulsion polymerized acrylic latex polymer.

In certain embodiments, the resin system of the present invention may be formulated using up to about 100 wt-% of such an emulsion polymerized acrylic latex polymer, with about 75 wt-% to about 100 wt-% (by weight of the total solids of the resin system) being presently preferred.

It has also been found that acrylic-containing polymers in the form acrylic-acrylate polymers can be used to produce coating compositions of the invention exhibiting excellent coating performance when used in medicament-contact coating applications such as MDT coatings. Examples of suitable acrylic-acrylate polymers are described, in part, in U.S. Pat. No. 7,189,787. For example, a suitable water-dispersible acrylic-acrylate copolymer may be formed by:
(i) providing an oxirane-functional acrylic polymer having an oxirane functionality of about 0.5 to 5;
(ii) providing an acid-functional acrylic polymer having an acid number of 30 to 500; and
(iii) reacting the oxirane-functional acrylic polymer and the acid-functional acrylic polymer together in the presence of an amine, preferably a tertiary amine, to form a water-dispersible acrylic-acrylate copolymer.

In step (i) above, the oxirane-functional acrylic polymer preferably (a) has a $M_n$ of about 2,500 to about 20,000, and (b) is the reaction product of about 1 to about 10 wt-% of oxirane-functional monomer, 0 to 60 wt-% of hydroxy-functional monomer, and the balance other monomer. In step (ii) above, the acid-functional acrylic polymer preferably (a) has an acid number of about 30 to about 500, (b) has a $M_n$ of about 2,000 to about 15,000, and (c) is the reaction product of at least about 15 wt-% of acid-functional monomer. In step (iii) above, the weight ratio of the oxirane-functional acrylic polymer to acid-functional acrylic polymer is preferably from about 90:10 to about 50:50 and the ratio of amine to oxirane groups is preferably about 0.8:1 to about 5:1.

It is also within the scope of the present invention to employ an acrylic-containing polymer in the form of a polyester-acrylate copolymer. U.S. Pat. App. No. 2005/0196629 describes, in part, suitable polyester-acrylate copolymers. By way of example, a suitable polyester-acrylate copolymer may be formed by grafting acrylic component onto an unsaturated polyester using one or more free radical initiators such as benzoyl peroxide. The unsaturation may be included in the polyester using any suitable compound, including, for example, maleic acid and/or anhydride. Preferably, the polyester-acrylate copolymer includes a sufficient amount of acid or anhydride groups to facilitate formation of a suitable amount of salt groups to disperse the copolymer in aqueous carriers.

It is also within the scope of the invention for the resin system to include a blend of a water-dispersible acrylic-containing polymer of the invention and a suitable fluoropolymer. Suitable water-dispersible fluoropolymers are described in the MDI-coatings art. See, for example, U.S. Pat. App. No. 2003/0121793. The relative concentrations of acrylic-containing polymer and fluoropolymer in the resin system may vary widely depending upon a variety of factors, though, the resin system preferably includes a majority of acrylic-containing polymer based on wt-%. In certain embodiments, the weight ratio of acrylic-containing polymer to fluoropolymer ranges from about 1.5:1 to about 100:1 (acrylic:fluoropolymer), and in a presently preferred embodiment the weight ratio is at least about 3:1, preferably about 3:1.

In certain preferred embodiments, the resin system of the invention is a water-dispersible self-crosslinking resin system (i.e., a resin system in which crosslinking occurs without the addition of a crosslinker). For example, it is possible to formulate coating compositions including certain of the acrylic-acrylate polymers described above, the emulsion polymerized acrylic latex polymer described above, or the epoxy-acrylate copolymer described above, which do not require the use of external crosslinkers. In some embodiments, however, the coating composition may benefit from the inclusion of one or more optional crosslinkers. Any suitable crosslinker (or combination of crosslinkers) may be employed in any suitable amount to achieve a desired level of crosslinking. For example, phenolic crosslinkers (e.g., phenoplasts), amino crosslinkers (e.g., aminoplasts), and combinations thereof, may be used. The crosslinker may be water-soluble, water-dispersible, organo-dispersible, and/or organosoluble (i.e., readily soluble in an organic solvent).

The concentration of crosslinker may vary widely depending upon the particular resin system employed, the desired coating or film property, and/or the particular crosslinker (or crosslinkers) used. In some embodiments, the coating composition preferably contains between about 0.01 wt-% and about 40 wt-%, more preferably between 0.25 wt-% and about 10 wt-%, and even more preferably between about 0.5 wt-% and about 5 wt.-% of crosslinker, by weight of nonvolatile material in the coating composition.

Examples of suitable phenolic crosslinkers (e.g., phenoplasts) include the reaction products of aldehydes with phenols. Formaldehyde and acetaldehyde are preferred aldehydes. Examples of suitable phenols that can be employed include phenol, cresol, p-phenylphenol, p-tert-butylphenol, p-tert-amylphenol, cyclopentylphenol, cresylic acid, BPA, and combinations thereof. Examples of suitable commercially available phenolic compounds include BAKELITE 6535LB, 6581 LB, and 6812LB (each available from Hexion Specialty Chemicals GmbH), DUREZ 33162 (Durez Corporation, Addison, Tex.), PHENODUR PR 285 55/IB/B and PR 897 (each available from CYTEC Surface Specialties, Smyrna, Ga.), and SANTOLINK EP.

Amino crosslinker resins (e.g., aminoplasts) are typically the condensation products of aldehydes (e.g., such as formaldehyde, acetaldehyde, crotonaldehyde, and benzaldehyde) with amino- or amido-group-containing substances (e.g., urea, melamine and benzoguanamine). Suitable amino crosslinking resins include, for example, benzoguanamine-formaldehyde-based resins, melamine-formaldehyde-based resins (e.g., hexamethonymethyl melamine), etherified melamine-formaldehyde, and urea-formaldehyde-based resins.

Condensation products of other amines and amides can also be employed such as, for example, aldehyde condensates of triazines, diazines, triazoles, guanidines, guanamines and alkyl- and aryl-substituted melamines. Some examples of such compounds are N,N'-dimethyl urea, benzourea, dicyandimide, formaguanamine, acetoguanamine, glycoluril, ammelin 2-chloro-4,6-diamino-1,3,5-triazine, 6-methyl-2,4-diamino-1,3,5-triazine, 3,5-diaminotriazole, triaminopyrimidine, 2-mercapto-4,6-diaminopyrimidine, 3,4,6-tris(ethylamino)-1,3,5-triazine, and the like. While the aldehyde employed is typically formaldehyde, other similar condensation products can be made from other aldehydes, such as acetaldehyde, crotonaldehyde, acrolein, benzaldehyde, furfural, glyoxal and the like.

Suitable commercially available amino crosslinking resins include, for example, CYMEL 301, CYMEL 303, CYMEL 370, CYMEL 373, CYMEL 1131, CYMEL 1125, CYMEL 1156, and CYMEL 5010 (all commercially available from Cytec Industries Inc., West Patterson, N.J.).

The coating composition can optionally include one or more additional polymers. In certain preferred embodiments, the one or more additional polymers are high-molecular-weight polymers (e.g., polymers having a $M_n$ of between about 4,000 and about 2,000,000, more preferably polymers having a $M_n$ of between about 20,000 and about 200,000, and even more preferably polymers having a $M_n$ of between about 40,000 and about 80,000). Non-limiting examples of suitable polymers may include acrylics, phenoxies, vinyls and the like, and combinations and copolymers thereof. While not presently preferred, polymers having molecular weights outside the aforementioned ranges may be included in the coating composition.

In certain preferred embodiments, the one or more additional polymers include one or more acrylic polymers, which are preferably high-molecular-weight acrylic polymers. These optional acrylic polymers, if present, are in addition to the aforementioned acrylic-containing polymer. In certain embodiments where the acrylic-containing polymer is an epoxy-acrylate polymer, the optional acrylic polymer is preferably prepared from monomers that are essentially non-reactive with the epoxy component or any carboxylic acid moiety present on the epoxy-acrylate polymer. Examples of suitable ethylenically unsaturated monomers include vinyl compounds, (meth)acrylate compounds, acrylamides, acrylonitriles and the like, and mixtures thereof. Suitable vinyl compounds useful in preparation of the optional acrylic resin include, for example, vinyl toluene, vinyl acetate, vinyl chloride, vinylidene chloride, styrene, substituted styrenes and the like, and mixtures thereof. Suitable (meth)acrylate compounds include butyl acrylate, ethyl acrylate, 2-ethylhexyl acrylate, isobutyl acrylate, tert-butyl acrylate, methyl acrylate, 2-hydroxyethyl acrylate, poly(ethylene glycol)acrylate, isobornyl acrylate, butyl methacrylate, methyl methacrylate, ethyl methacrylate, isobutyl methacrylate, 2-hydroxyethyl methacrylate, poly(ethylene glycol)methacrylate, poly(propylene glycol)methacrylate and the like, and mixtures thereof. Styrene and butyl acrylate are preferred monomers for forming the optional acrylic polymer. In some embodiments, a small amount of monomers that can undergo reaction with the epoxy component may be used (e.g., g., hydroxy monomers such as 2-hydroxy ethylmethacrylate, amide monomers such as acrylamide, and N-methylol monomers such as N-methylol acrylamide).

As discussed above, the optional acrylic polymer is preferably a high-molecular-weight acrylic polymer. In preferred embodiments, the optional acrylic polymer has a $M_n$ of at least about 20,000, more preferably at least about 30,000, and even more preferably at least about 40,000. Preferably, the optional acrylic polymer has a $M_n$ of less than about 2,000,000, more preferably less than about 200,000, and even more preferably less than about 80,000.

The optional acrylic polymer can be introduced into the coating composition at any convenient stage of preparation. For example, in a certain preferred embodiment, the optional acrylic polymer (if present) is prepared in situ in the presence of an aqueous dispersion of an epoxy-acrylate polymer described herein. While not intending to be bound by theory, when the optional acrylic polymer is formed in situ, the resulting polymer may form an interpenetrating network with the epoxy-acrylate polymer and/or any other acrylic-containing polymer employed. The optional acrylic polymer can also be introduced as a preformed polymer during any convenient stage of preparation.

As described, in part, in U.S. Pat. No. 7,037,584, in some embodiments, the monomers used to form the optional acrylic polymer may (prior to polymerization) function as reactive diluent capable of reducing an amount of volatile organic compound (VOCs) used to form a coating composition. In such embodiments, the reactive diluent preferably functions as a solvent or otherwise lowers the viscosity of the blend of reactants. Presently preferred reactive diluents include styrene and butyl acrylate. The use of one or more reactive diluents as a "solvent" can eliminate or reduce the need to incorporate a substantial amount of other cosolvents (such as butanol) during processing.

The resin system may be dissolved in a suitable solvent to form a coating composition of the invention, or may be blended with water and/or a suitable solvent to form a coating dispersion. The resin system is preferably combined with an aqueous carrier to form an aqueous coating dispersion or solution. If desired, the coating composition may contain one or more organic solvents. For certain water-based coating compositions, one or more organic solvents may be incorporated in a suitable amount into the coating compositions to facilitate wetting out of the substrate and coalescence of the coating composition into a continuous film.

In presently preferred embodiments, at least about 50 wt-% of the liquid carrier system is water, more preferably 60 wt-% is water, and even more preferably 75 wt-% is water.

Certain preferred coating compositions of the invention include at least about 10 wt-% of water (typically from about 10 wt-% of water up to about 80 wt-% of water), more preferably at least about 20 wt-% of water, and even more preferably at least about 40 wt-% of water (in some embodiment about 50 wt-% or more of water), based on the total weight of the coating composition.

The coating compositions may optionally include any other suitable additives that do not adversely affect the coating composition or a cured coating resulting therefrom. Suitable additives include, for example, those that improve the processability or manufacturability of the composition, enhance composition aesthetics, or improve a particular functional property or characteristic of the composition, such as adhesion of the cured composition to a substrate. Additives that may be included are carriers, emulsifiers, pigments, metal powders or paste, fillers, anti-migration aids, anti-microbials, extenders, curing agents, lubricants, coalescents, wetting agents, biocides, plasticizers, antifoaming agents, colorants, waxes, anti-oxidants, anticorrosion agents, flow control agents, thixotropic agents, dispersants, adhesion promoters, scavenger agents, or combinations thereof. Each optional ingredient can be included in a sufficient amount to serve its intended purpose, but preferably not in such an amount to adversely affect a coating composition or a cured coating composition resulting therefrom.

The amount of solids included in the coating compositions may vary widely depending upon a variety of factors including, for example, the method of coating application and the ingredients used to form the coating composition. In certain non-pigmented embodiments, the coating composition of the invention preferably include at least about 10, more preferably at least about 15, and even more preferably at least about 20 wt-% of solids, based on the total weight of coating composition. In certain non-pigmented embodiments, the coating composition preferably include less than about 50, more preferably less than about 40, and even more preferably less than about 30 wt-% of solids, based on the total weight of the coating composition. When pigment is included in the coating composition, the total amount of solids may exceed those levels discussed above.

In another aspect, the coating composition of the invention is applied to at least a portion of a substrate to form a coated article. The substrate may be any suitable type of substrate including, for example, metal (e.g., aluminum, steel, etc.), glass, plastic, or ceramic. To ensure optimal coating performance, the coating composition is preferably applied to a suitably clean substrate. The substrate surface upon which the coating composition is to be applied is preferably free of unsuitable amounts of residual organic compounds. For example, metal containers such as aluminum MDI cans, often include amounts of residual organic compounds such as, for example, lubricants used in forming the metal containers from planar metal stock (e.g., coil or sheet). Such residual organic compounds, if present in an unsuitable amount, may adversely affect coating properties such as adhesion of the coating to the underlying substrate.

In particular, for a water-based coating composition of the invention, the substrate is preferably suitably clean to achieve efficient wetting out of the substrate upon application of the coating composition to form a continuous film. Examples of useful measures for assessing the cleanliness of a substrate surface include the surface energy of the surface and/or the amount of organic compound capable of being extracted (e.g., using solvent washes) from the surface. While not intending to be bound by theory, surfaces (e.g., metal surfaces such as aluminum) with substantial amounts of residual organic compounds tend to have a surface energy that is too low for most aqueous coating compositions to efficiently wet out the surface.

Surface pretreatments are known for producing suitably clean substrate surfaces. An example of a suitably clean surface is a cleaned substrate surface obtained using the methods described in U.S. Pat. No. 7,205,026 by Groeger et al., which discloses a cleaning process whereby an aluminum substrate (in the form of deep drawn aluminum canisters) is cleaned with an aliphatic hydrocarbon degreaser and surfactant, followed with a series of rinses with deionized water and then preferably light anodization. Such cleaning processes are also discussed in U.S. Pat. App. No. 2006/0083879.

The cleaning process developed by Presspart and described in U.S. patent application Ser. No. 11/952,652 filed on Dec. 7, 2007 by Groeger, et al. and published as US20090145427 entitled "Method for Applying a Polymer Coating to an Internal Surface of a Container" (which is incorporated herein by reference in its entirety) is a presently preferred process for producing a suitably clean substrate surface. The Presspart cleaning process uses an aqueous cleaning composition that includes (i) an anionic surfactant and an emulsifier and (ii) optionally one or more of an alkaline salt (e.g., sodium carbonate), a buffer, and preferably a metal chelating agent (e.g., sodium phosphate, ethylenediamene tetraacetic acid, porphine, nitrilo triacetate, and ethylenediamene). Additional information pertaining to the Presspart cleaning process is provided below.

Suitable anionic surfactants for use in the cleaning composition of the Presspart cleaning process include sodium dodecylbenzene sulfonate, alkyl phosphate, alkyl sulfonate, alkyl benzenesulfonate, and sodium di(2-ethylhexyl) sulfosuccinate, with dodecylbenzene sulfonate being particularly preferred. The anionic surfactant is used to penetrate the oil film on the deep drawn cans and to emulsify and disperse the oil in the cleaning bath.

The emulsifier is used to suspend oil drops in the cleaning solution. A preferred emulsifier is tetrasodium phosphate, which also serves as a pH buffer to extend the cleaning solution stability.

The Presspart cleaning process typically includes two or three sequential cleaning baths including the cleaning composition. The cleaning baths are preferably maintained at a temperature of from about 25° C. to about 60° C., and more preferably at about 50° C. The pH of the cleaning baths is preferably from about 9 to about 9.8, more preferably about 9.2. Water used to prepare the wash solutions of the cleaning baths preferably has a conductivity below about 200 µS/cm and the hardness is preferably controlled to 0 on the German Hardness scale. MDI canisters are typically immersed in each bath for period of about 1 to 5 minutes, more preferably for about 2 minutes. The cleaning baths may be ultrasonically agitated between about 30 kHz and about 43 kHz, for example, and more preferably at about 40 kHz with superimposed sweep frequency of 1 kHz. Oil separation technology may be applied and fresh cleaning solution may be added on a controlled basis for each tray that is filled with MDI canisters.

Cleaning is followed by several rinse baths, which may include three or four sequential rinse baths. The first may or may not be ultrasonically agitated, but is preferably agitated. The rinse baths are maintained at a temperature of from about 18 to about 27° C., but most preferably at about 25° C. Water hardness is controlled by conductivity measurement to below 50 µS/cm with hardness of 0 on the German Hardness scale. A final rinse bath preferably consists of deionized water, controlled to conductivity between 4 and 20 µS/cm, more preferably at 5-10 µS/cm with hardness controlled to 0 on the German Hardness scale. This bath typically has a pH range from about 5.8 to 7.0, more preferably about 6.8, and a bath temperature between about 18 and 27° C., more preferably about 25° C. The cleaned substrate surfaces may then be dried, e.g., in filtered air in a laminar flow oven.

Aluminum MDI containers cleaned using the Presspart cleaning process were analyzed by Presspart via gas chromatography/mass spectrometry ("GC/MS") analysis to assay the amount of residual organic extractibles present on the cleaned inner surface. The cleaned MDI containers were analyzed and found to have the following surface properties.

TABLE 1

Total Organic Extractibles

| Sampling Method | Total Organics Detected |
|---|---|
| Thermal desorption (ramp to 320° C.) | <1 ppm |
| Ethanol extraction | <1 ppm |
| Methylene chloride extraction | <1 ppm |

Wetting behavior of the cleaned MDI container surfaces was also determined by contact angle measurement. The surface energy of the cleaned MDI container surface was from about 60 to about 72 dyne-cm, and more preferably from about 68 to about 70 dyne-cm.

Presently preferred MDI containers have a suitably clean inner surface that, prior to coating with the coating composition of the invention, exhibit the aforementioned cleanliness properties, independent of the particular cleaning process employed.

The coating composition of the present invention may be applied to any desired thickness on a suitably clean substrate and may utilize any desired number of coating layers. In presently preferred embodiments, the resulting cured coatings exhibit an average coating thickness of from about 1 to about 30 microns, and more preferably from about 10 to about 20 microns.

Coatings of the invention may be monolayer coatings (i.e., coatings formed from a single application of coating composition) or multi-layer coatings (i.e., coatings formed from two or more applications of coating composition, which may be the same or different). In a presently preferred embodiment, a monolayer coating is employed. In some embodiments, two or more layers of the coating composition of the invention may be applied.

Although not presently preferred, it is contemplated that one or more other polymer coating layers (e.g., one or more primer or base layers) may be applied to a substrate prior to application of the coating composition of the invention. Similarly, while not presently preferred, it is contemplated that one or more topcoats may be applied to the coating composition of the invention.

In another aspect, the invention also provides a method of coating an article or a portion thereof. The method includes forming a composition described herein and applying the composition to a substrate prior to, or after, forming the substrate into an article such as an MDI container. Although any suitable substrate may be employed, the substrate is typically a metal used in the pharmaceutical packaging industry such as, for example, aluminum.

The coating composition may be applied to a substrate using any suitable method such as, for example, spray coating, coil coating, roll coating, dip coating, powder coating, and via direct application techniques using, for example, a brush or sponge. Spray coating is a presently preferred method of application.

In the case of MDI canisters, coatings are typically applied by spray application to coat the interior surface of the canister. Two types of spray guns are typically used: air-assisted and airless. Air-assisted spray guns are typically very adaptable and are easily plugged into compressed air sources. In some instances, however, the high airflow can cause coating defects and excess misting. Airless spray is more common for fixed industrial applications. In this method, the coating is typically compressed and forced through a nozzle at high speed. A variant of this method is hot airless spray, which involves the use of a coating pre-heater to allow higher solids and/or higher viscosity coatings to be spray applied. Pressures in excess of 1,000 psi can typically be used for this type of coating process. In addition to the aforementioned spray techniques, it is contemplated that any suitable application technique may be used to apply the coating compositions of the invention to MDI canisters.

After application to a substrate, the coating composition is preferably cured to remove solvent and form an adherent cured coating, which is preferably a crosslinked adherent coating. Any suitable curing process can be employed, including, for example, oven baking by either conventional or convectional methods. The curing process may be performed in either discrete or combined steps. For example, substrates can be dried at ambient or elevated temperature to leave the coating compositions in a largely un-crosslinked state. The coated substrates can then be heated to fully cure the composition. In certain instances, coating compositions can be dried and cured in one step.

The curing process may be performed at any suitable temperature for any suitable period of time sufficient to achieve the desired result. The temperatures of the curing process may depend on the speed of the coating process, heat transfer conditions, and/or other factors in order to obtain the desired cure of the coating.

The invention also provides coated articles including, for example, coated articles useful for storing and/or administering medicaments. Preferably, all, or substantially all, of the internal surfaces that medicament may come into contact with are suitably coated. Coated articles useful for storing and/or administering medicaments generally include a container (such as, for example, a metal can), which is in communication with a cap and/or a metering unit comprising a valve for dispensing medicament. Non-limiting examples of such articles include dry powder inhalers (DPIs), MDIs (including, e.g., both pMDIs and non-pressurized MDIs). The coating composition of the invention may also be used on other articles having one or more medicament-contact surfaces such as, for example, metal canisters (e.g., for storing or administering medicament), collapsible metallic medicament-dispensing tubes (e.g., ointment tubes), and metallic or glass drug vials (e.g., metallic or glass drug vials for use in storing protein-based medicaments).

As previously discussed, coating compositions of the invention are particularly useful for coating one or more medicament-contact surfaces of MDIs. In preferred embodiments, the coating composition is used to coat the inner surface of an MDI container. MDI containers are typically metal cans formed via deep drawing (e.g., via draw re draw processes) or impact extrusion operation. Aluminum (or an aluminum alloy) is typically the preferred metal for forming metal MDI cans. In a presently preferred embodiment, the coating composition is spray applied to the inside surface of MDI cans. It is also contemplated that the coating composition may be used to coat components of the metering unit, as well as any other surfaces of the MD1 device that may come into contact with medicament.

Certain preferred embodiments of the coatings of the invention are particularly suited for prolonged contact with medicaments intended for internal use by humans and, more preferably, internal use by humans through inhalation.

EXAMPLES

The present invention is illustrated by the following examples. It is to be understood that the particular examples, materials, amounts, and procedures are to be interpreted broadly in accordance with the scope and spirit of the invention as set forth herein. Unless otherwise indicated, all parts and percentages are by weight and all molecular weights are weight average molecular weight. Unless otherwise specified, all chemicals used are commercially available from, for example, Sigma-Aldrich, St. Louis, Mo.

Example 1: Preparation of an Acid-Functional Acrylic Prepolymer

A flask was equipped with a stirrer, reflux condenser, thermocouple, heating mantle, and nitrogen blanket. Into the flask was added 275.2 parts deionized water, 2550.3 parts amyl alcohol and 173.2 parts hexyl cellosolve. The contents of the flask were heated to 98° C. In a separate vessel were combined 1329.4 parts acrylic acid, 973.9 parts ethyl acrylate, 855.1 parts methacrylic acid, 1711.2 parts styrene and 385.2 parts of 75% solid benzoyl peroxide in water. The vessel was stirred to uniformly mix the ingredients to form a premix. When the premix was uniform and the flask was at 98° C., the contents of the premix vessel were added to the flask uniformly over 2 hours while maintaining the temperature at 98° C. to 103° C. When the addition was complete, the flask was held at 94° C. to 97° C. for an additional 2 hours. After the 2-hour hold, the heat was removed and 1237.8 parts amyl alcohol and 508.7 parts butanol were added. When cooled, the acrylic prepolymer solids were 51.2%+/−1.0% with an acid number between 290 and 320 and a viscosity between 6,000 and 16,000 centipoise.

Example 2: Preparation of a Water-Based Epoxy-Acrylate Coating Composition

A flask was equipped with a stirrer, reflux condenser, thermocouple, heating mantle, and nitrogen blanket. Into the flask was added 1006.9 parts EPON 828, 548.8 parts Bisphenol A, 172.9 parts butyl cellosolve and 2.5 parts tri-n-butylamine. The contents of the flask were heated to 130° C. and then allowed to exotherm to a maximum of 188° C. After the exotherm, the batch was maintained at 160° C. until a maximum epoxy value of 0.040 was achieved. When this epoxy value was achieved, 39.2 parts hexyl cellosolve, 20.8 parts butyl cellosolve, and 159.1 parts butanol were slowly added and the temperature cooled to less than 132° C. At 132° C., 1347.12 parts of the acrylic prepolymer of Example 1 was added. The contents of the flask were then adjusted to 110° C. Once the contents were at 110° C., 100.3 parts of dimethyl ethanolamine were added. The contents were held at 110° C. for 1 hour at which time 47.8 parts of dimethyl ethanolamine were added. After the dimethyl ethanolamine addition, the contents were stirred for 15 minutes, and then 5545.3 parts of deionized water were added slowly. When the addition of the water was complete, the contents were heated to 80° C. over 1 hour. When the 1-hour period was over, 387.6 parts styrene, 385.0 parts butyl acrylate, and 7.8 parts benzoin were added to the flask. When the contents were at 80° C., 7.8 parts of a 35% solution of hydrogen peroxide and 12.1 parts of deionized water were added to the flask. The contents of the flask were then allowed to exotherm to a maximum of 87° C. and held for 2 hours. After the 2-hour holding period, 193.8 parts styrene, 1.9 parts benzoin, 2.0 parts 35% solution hydrogen peroxide and 11.0 parts deionized water were added to the flask. The contents of the flask were held at 86° C. for 4 hours, and then cooled to 38° C. 3804.1 parts of deionized water were then added to the flask, followed by 22.6 parts dimethyl ethanolamine, 992.6 parts butyl cellosolve, and 437.4 parts butanol. The resulting composition was allowed to cool. The composition was then adjusted with deionized water and dimethyl ethanolamine to yield a coating composition having solids content of 20.0% solids and a viscosity of 66 second using a #2 Ford cup.

Example 3: Preparation of a Coated Substrate

The water-based epoxy-acrylate coating composition of Example 2 was used to coat cleaned aluminum MDI canisters produced by Presspart Inc. of Cary, N.C. Hot airless lance spray application equipment was used to spray apply the coating composition of Example 2 onto the inside surface of the MDI canisters. The spray parameters were varied to produce coatings of different coating thicknesses. The final coating thickness applied to the MDI canisters ranged from between 1 and 20 microns, with 5 to 10 microns being preferred. A typical coating weight used in this testing was about 130 mg (milligrams) per canister. The coatings were cured by passing the MDI canisters through a multi-zone electrically heated oven. Bake conditions were varied, ranging from between about 200° C. and about 400° C. for about 5 to about 15 minutes, with preferred conditions being about 210° C. to about 230° C. for about 10 minutes.

Example 4: Coating Performance

The water-based epoxy-acrylate coating of Example 3 provided good coverage of the metal substrate without visible defects such as sagging, blistering or eye-holing. Coating integrity was further confirmed by filling the coated containers of Example 3 with an acidified copper sulfate solution (about 0.2 wt-% copper sulfate in water, acidified slightly by addition of about 0.02 wt-% of hydrochloric acid) for a short period of time (typically about a minute), emptying the solution out of the container and then subsequently visually inspecting the coated surface, looking for any discoloration caused by reaction of any exposed aluminum with the solution. The cured coatings of Example 3 were observed to exhibit suitable coating coverage upon such visual inspection. Coating integrity for the cured coatings of Example 3 was further confirmed by measurement of metal exposure using a Wilkins Anderson Company (WACO) Enamel Rater instrument and test method (6.3 Volts DC; cans were completely filled with a 10 wt-% sodium chloride solution dissolved in deionized water and tested for 4 seconds). Metal exposure for the coated canisters of Example 3 was found to range from about 0 to about 20 mA (milliamps), and for some preferred examples from about 0-5. In addition, the cured coatings exhibited suitable levels of both adhesion and flexibility.

Coated canisters of Example 3 were packed with appropriate medicaments to simulate pMDI medicaments and tested for drug stability, drug release, and drug retention. In these tests, the coated canisters of Example 3 showed commercially acceptable levels of performance when compared with control cans coated with solvent-based fluorinated polymer coatings. The coated canisters of Example 3 showed no interaction issues or performance defects when packed with a mixture of 15% ethanol and hydrofluoroalkane (HFA) propellant and stored for 6 months. Suitable propellant compatibility was also observed for CFC and HFC propellants. Propellant compatibility was assessed through both (i) observations to detect any structural changes in the coating (e.g., changes in color, transparency, swelling, loss of adhesion, etc.) and (ii) GC/MS analysis to identify any polymer fragments from the coating present in the propellant.

When packing medicaments for human or animal consumption (e.g., such as MDIs), it is highly desirable that there are minimal amounts of coating material extracted from the coating into the package contents. The coated canisters of Example 3 showed acceptably low levels of migration (i.e., non-detectable) when tested in laboratory simulation testing used to predict subsequent pack test performance. In these tests, 10 coated canisters of Example 3 were filled with ethanol and stored at 60° C. for 30 days to promote migration of any coating constituents. The ethanol extracted from all 10 coated canisters was then combined, concentrated 100 to 1, and direct injected into a Gas Chromatograph Mass Spectrometer (GC/MS) for detection of extracted coating material.

Example 5: Additional Examples

In addition to the epoxy-acrylate coating composition of Example 2, the MDI coating performance was also assessed for water-based coating compositions including one of the following water-dispersible resinous binder systems:
(i) an acrylic-acrylate polymer of the invention;
(ii) an emulsion polymerized acrylic latex polymer of the invention; and
(iii) the emulsion polymerized acrylic latex polymer of (ii) mixed with conventional fluoropolymer in a 3:1 weight ratio (acrylic latex polymer:fluoropolymer).

Each of the water-based coating compositions was directly applied to an inner aluminum medicament-contact surface of a Presspart MDI canister, which had been cleaned by Presspart using the Presspart cleaning process. After being suitably cured, each of the cured coating compositions exhibited a suitable balance of MDI coating performance attributes (i.e., good flexibility, good adhesion, good drug compatibility, good propellant compatibility, non-detectable level of extractibles, etc.), which were generally comparable to that of the cured epoxy-acrylate coating of Example 2.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:
1. A coated article, comprising:
a pressurized metered dose inhaler, comprising:
a pressurized container filled with a propellant-based medicament composition including a drug and a liquefied gas propellant, wherein the pressurized container has a coating applied on at least a portion of an interior metal surface such that the coating is in contact with the medicament composition; and
wherein the coating is formed from an aqueous coating composition that comprises a water-dispersible resin system that includes at least about 10% by weight, based on total solids, of an emulsion polymerized acrylic latex polymer, and wherein the aqueous coating composition is substantially free of bound BPA and aromatic glycidyl ether compounds.

2. The coated article of claim 1, wherein the liquefied gas propellant comprises a hydrofluoroalkane, a chlorofluorocarbon, a hydrofluorocarbon, or a combination thereof.

3. The coated article of claim 1, wherein the interior metal surface comprises aluminum.

4. The coated article of claim 1, wherein the resin system, based on total solids, comprises from about 50% to about 100% by weight of acrylic.

5. The coated article of claim 1, wherein the emulsion polymerized acrylic latex polymer comprises a reaction product of ethylenically unsaturated acid or anhydride monomers.

6. The coated article of claim 1, wherein the coating composition further comprises a co-resin selected from a polyester polymer, a fluoropolymer, an epoxy polymer, a phenolic resin, a vinyl chloride polymer, an acrylic polymer, or a combination thereof.

7. The coated article of claim 1, wherein the emulsion polymerized latex polymer comprises a reaction product of reactants including:
(i) an acid- or anhydride-functional acrylic polymer;
(ii) a mixture of ethylenically unsaturated monomers including at least one oxirane-functional monomer; and
(iii) an amine.

8. The coated article of claim 1, wherein the emulsion polymerized acrylic latex polymer includes an acrylic component formed from an acrylic monomer mixture including a (meth)acrylic acid ester, an ethylenically unsaturated mono- or multi-functional acid or anhydride, and a vinyl compound.

9. The coated article of claim 8, wherein the acrylic monomer mixture includes an acrylic and/or methacrylic acid, styrene, and ethyl acrylate.

10. The coated article of claim 1, wherein the medicament comprises albuterol, salmeterol, or budesonide.

11. The coated article of claim 10, wherein the liquefied gas propellant comprises a hydrofluoroalkane, a chlorofluorocarbon, a hydrofluorocarbon, or a combination thereof.

12. The coated article of claim 1, wherein the metal can comprises a deep drawn metal can, and wherein the coating has an average coating thickness of from 1 to 30 microns.

13. The coated article of claim 1, wherein the coating is a monolayer coating having an average coating thickness of from about 10 to about 20 microns.

14. The coated article of claim 1, wherein:
the aqueous coating composition includes from at least 10 to less than 50 weight percent of solids, based on the total weight of the coating composition; and
water constitutes at least 50 weight percent of the liquid carrier system of the aqueous coating composition.

15. The coated article of claim 1, wherein the water-dispersible resin system includes about 75 weight percent to about 100 weight percent of the emulsion polymerized acrylic latex polymer, by weight of the total solids of the resin system.

16. The coated article of claim 1, wherein the water-dispersible resin system includes a fluoropolymer co-resin.

17. A coated article, comprising:
a pressurized metered dose inhaler, comprising:
a pressurized metal can having a coating that is substantially free of bound BPA and aromatic glycidyl ether compounds applied on at least a portion of an interior surface, wherein the coating is formed from an aqueous coating composition comprising a water-dispersible resin system that includes about 75 weight percent to about 100 weight percent of an emulsion polymerized acrylic latex polymer, by weight of the total solids of the resin system; wherein the pressurized metal can contains a medicament composition including:
a medicament that is a pulmonary or nasal medicament, a liquefied gas propellant.

18. The coated article of claim 17, wherein the liquefied gas propellant comprises a hydrofluoroalkane, a chlorofluorocarbon, a hydrofluorocarbon, or a combination thereof.

19. The coated article of claim 18, wherein the coating is a monolayer coating having an average coating thickness of from about 10 to about 20 microns.

20. A method, comprising:
providing a metered dose inhaler container comprising:
a metallic interior surface, and
an adherent polymer coating that is substantially free of bound BPA and aromatic glycidyl ether compounds applied to the metallic interior surface, the adherent polymer coating formed from an aqueous coating composition comprising a water-dispersible resin system that includes at least about 10% by weight, based on total solids, of an emulsion polymerized acrylic latex polymer; and
filling the container with a medicament composition including a medicament and a liquefied gas propellant so that the medicament composition is in contact with the adherent polymer coating.

21. The method of claim 20, wherein the liquefied gas propellant comprises a hydrofluoroalkane, a chlorofluorocarbon, a hydrofluorocarbon, or a combination thereof, and wherein the coating has an average coating thickness of from about 1 to about 30 microns.

* * * * *